US00PP22420P2

(12) United States Plant Patent
Cho

(10) Patent No.: US PP22,420 P2
(45) Date of Patent: Dec. 27, 2011

(54) ***COLOCASIA* PLANT NAMED 'KONA COFFEE'**

(50) Latin Name: *Colocasia esculenta*
Varietal Denomination: KONA COFFEE

(76) Inventor: John Cho, Paia, HI (US)

( * ) Notice: Subject to any disclaimer, the term of this patent is extended or adjusted under 35 U.S.C. 154(b) by 0 days.

(21) Appl. No.: 12/927,989

(22) Filed: Nov. 30, 2010

(51) Int. Cl.
*A01H 5/00* (2006.01)

(52) U.S. Cl. ..... Plt./373
(58) Field of Classification Search ..... Plt./373, Plt./226, 263.1
See application file for complete search history.

*Primary Examiner* — Kent L Bell

(57) ABSTRACT

A new cultivar of *Colocasia* plant named 'KONA COFFEE' that is characterized by a compact and branching habit with 4 to 7 lateral shoots, small dark purple to almost black colored leaves that are slightly cupped inwardly with a glossy finish and semi-glossy burgundy to dark burgundy colored petioles. In combination these characteristics distinguish 'KONA COFFEE' from all other varieties of *Colocasia* known to the inventor.

4 Drawing Sheets

Genus: *COLOCASIA.*
Species: *esculenta.*
Denomination: 'KONA COFFEE'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar named 'KONA COFFEE'.

*Colocasia* is a tuberous rooted perennial which is native to tropical Asia and Polynesia. It grows to 1.5-2 m in height from starchy tubers. The leaves of *Colocasia* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'KONA COFFEE' is the product of a formal breeding program carried out in a cultivated area in Kula, Hi. The purpose of the breeding program is to develop new commercial varieties by combining attributes not found in currently commercially available varieties.

'KONA COFFEE' is a seedling selection from the controlled pollination between the two unreleased and unpatented seedlings developed during the breeding program and known to the inventor as '2002-26' (female parent) and '2005-51' (male parent). Initially designated as '2006-111', 'KONA COFFEE' was selected from the resulting seedling population in 2006.

'KONA COFFEE' may be compared with its parents as follows:

'KONA COFFEE' bears glossy dark purple to almost black leaves. The leaves of the female parent are of similar color but matte in texture. A single plant of 'KONA COFFEE' is approximately one-quarter to one-third smaller in overall size in comparison with its female parent. The leaves of the male parent are dark green and glossy, with a slightly undulating margin. The leaves of the male parent are two to three times larger than the leaves of 'KONA COFFEE'.

The closest comparison variety known to the inventor is *Colocasia* 'Black Magic' (unpatented). Whereas 'KONA COFFEE' produces uniform dark purple to almost black colored leaves with a glossy finish, the leaves of 'Black Magic' are similarly dark purple to almost black but are smaller in size and have a matte appearance.

The most commonly employed means of asexual propagation of the genus *Colocasia* is the excision and replanting of a plant shoot which consists of the apical 1 cm-2 cm portion of the plant corm with the attached basal 15 cm-20 cm portion of the petiole. In regions of the world where *Colocasias* are grown, this plant shoot is known as a "huli", and the means of propagation is known as "huli propagation". The inventor first asexually propagated 'KONA COFFEE' by this method in 2006 is his growing grounds in Hawaii. Evaluation in field studies have shown the unique features of 'KONA COFFEE' to be stable, uniform, and to reproduce true to type in successive generations of asexual propagation.

SUMMARY OF THE INVENTION

The following traits have been repeatedly observed and represent the distinguishing characteristics of the new *Colocasia* variety named 'KONA COFFEE'. In combination these traits set 'KONA COFFEE' apart from all other varieties of *Colocasia* known to the inventor. 'KONA COFFEE' has not been tested under all possible conditions and phenotypic differences may be observed with variations in environmental, climatic and cultural conditions, however, without any variance in genotype:

1. 'KONA COFFEE' forms a small compact plant with 4 to 7 lateral shoots.
2. 'KONA COFFEE' exhibits small saggitate-shaped leaves and slightly undulating margins that are slightly inwardly cupped.
3. The leaves of 'KONA COFFEE' are dark purple to almost black in color with a small circular-shaped burgundy colored 'piko' (i.e. the adaxial point of attachment between the leaf blade and petiole).

4. The surface of the leaves of 'KONA COFFEE' is glossy in appearance.
5. 'KONA COFFEE' has semi-glossy burgundy to dark burgundy colored petioles.

BRIEF DESCRIPTION OF THE DRAWINGS

The accompanying color drawings

Figure 1:
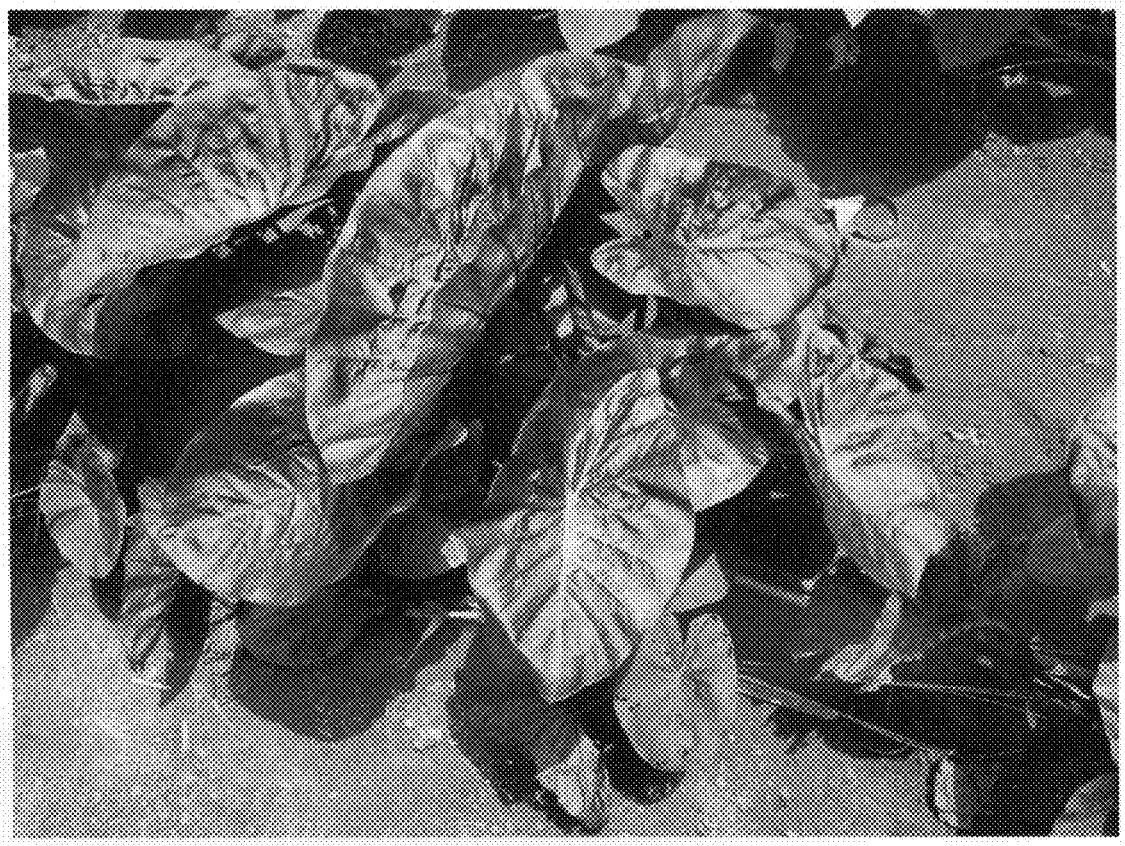
FIGS. 1 to 4 illustrate the overall appearance of 'KONA COFFEE' showing the colors as true as it is reasonably possible to obtain in colored reproductions of this type. Colors in the drawing may differ from the color values cited in the detailed botanical description, which accurately describe the actual colors of the new variety 'KONA COFFEE'.

The drawing labeled as FIG. 1 shows a plant of 'KONA COFFEE' grown from a huli after approximately 3 months.

Figure 2:
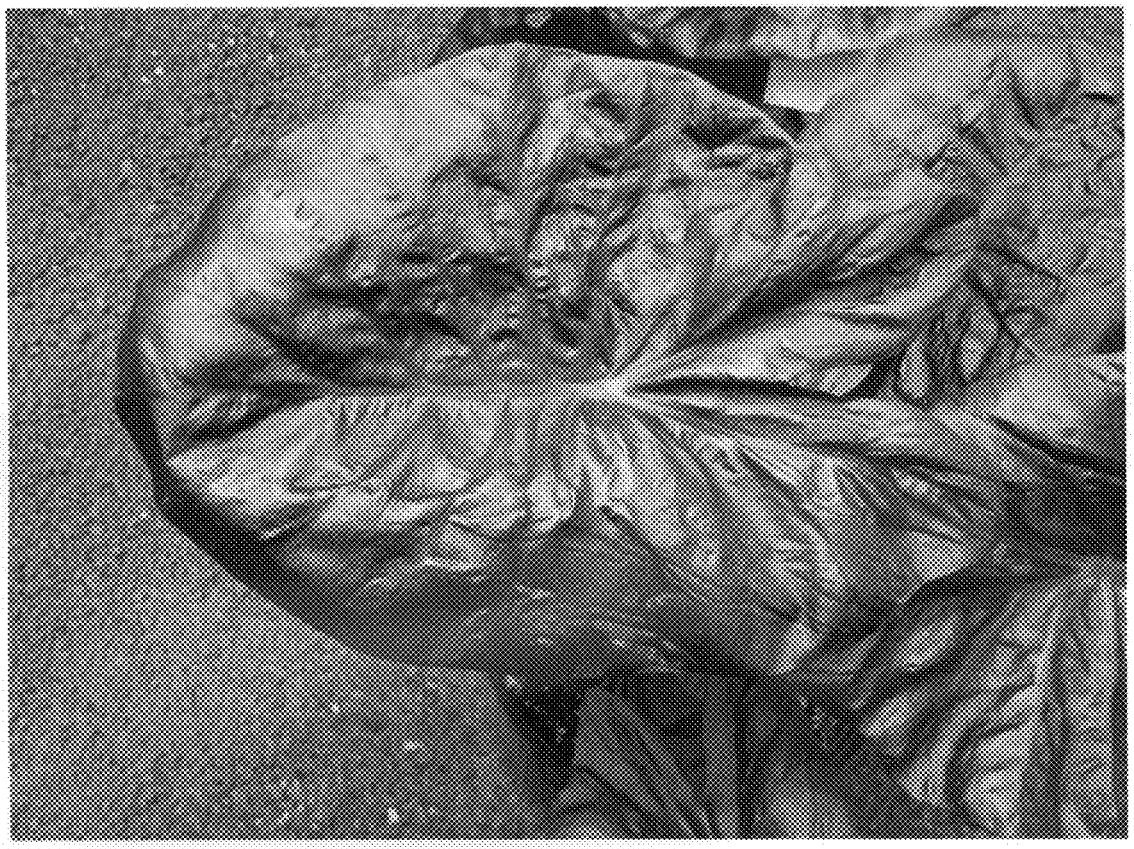

The drawing labeled FIG. 2 illustrates a mature leaf of 'KONA COFFEE' with its characteristic inward cupping, dark purple to black coloration, glossy surface texture and small burgundy colored piko.

Figure 3:
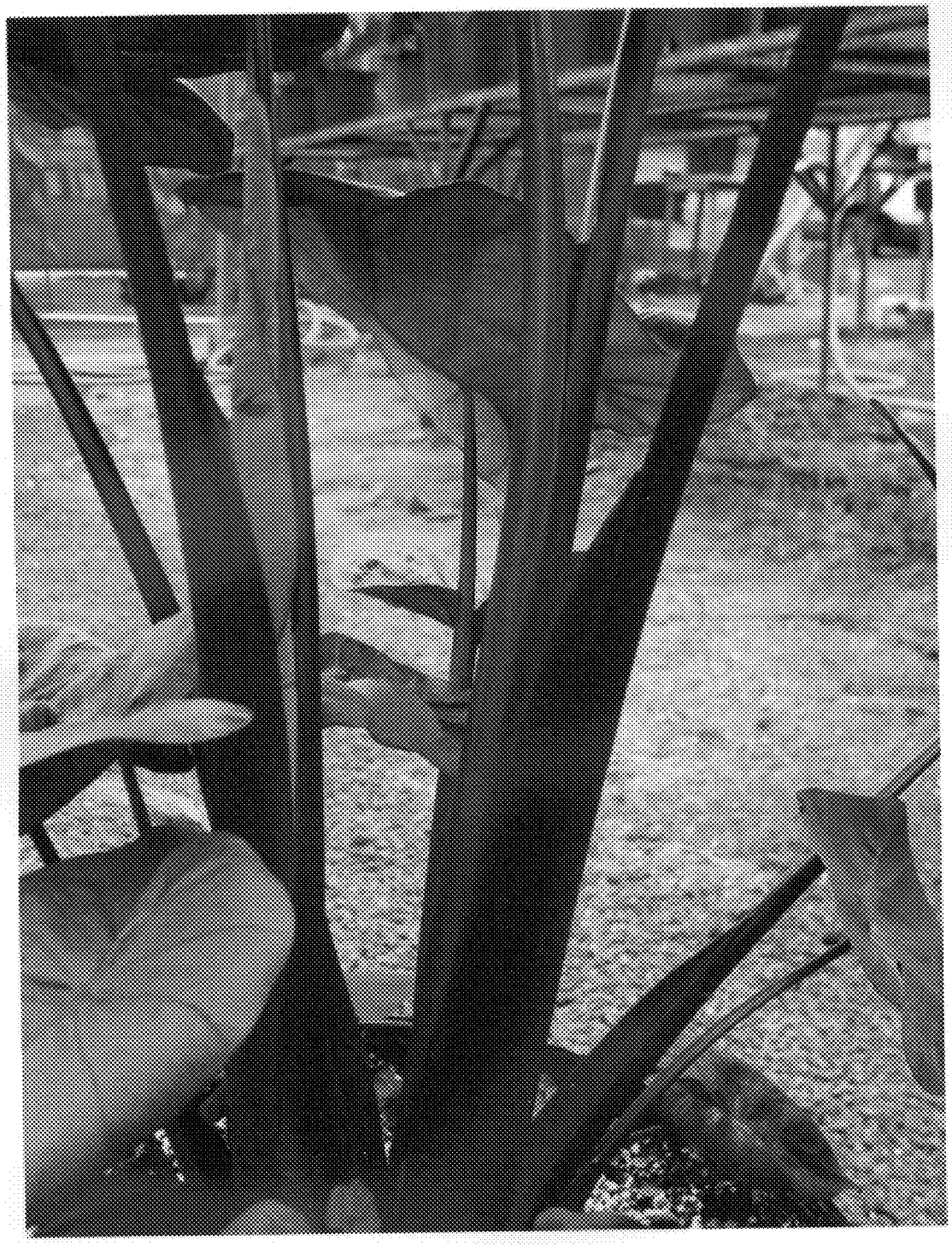

The drawing labeled as FIG. 3 shows the semi glossy burgundy colored petioles of 'KONA COFFEE'.

Figure 4:
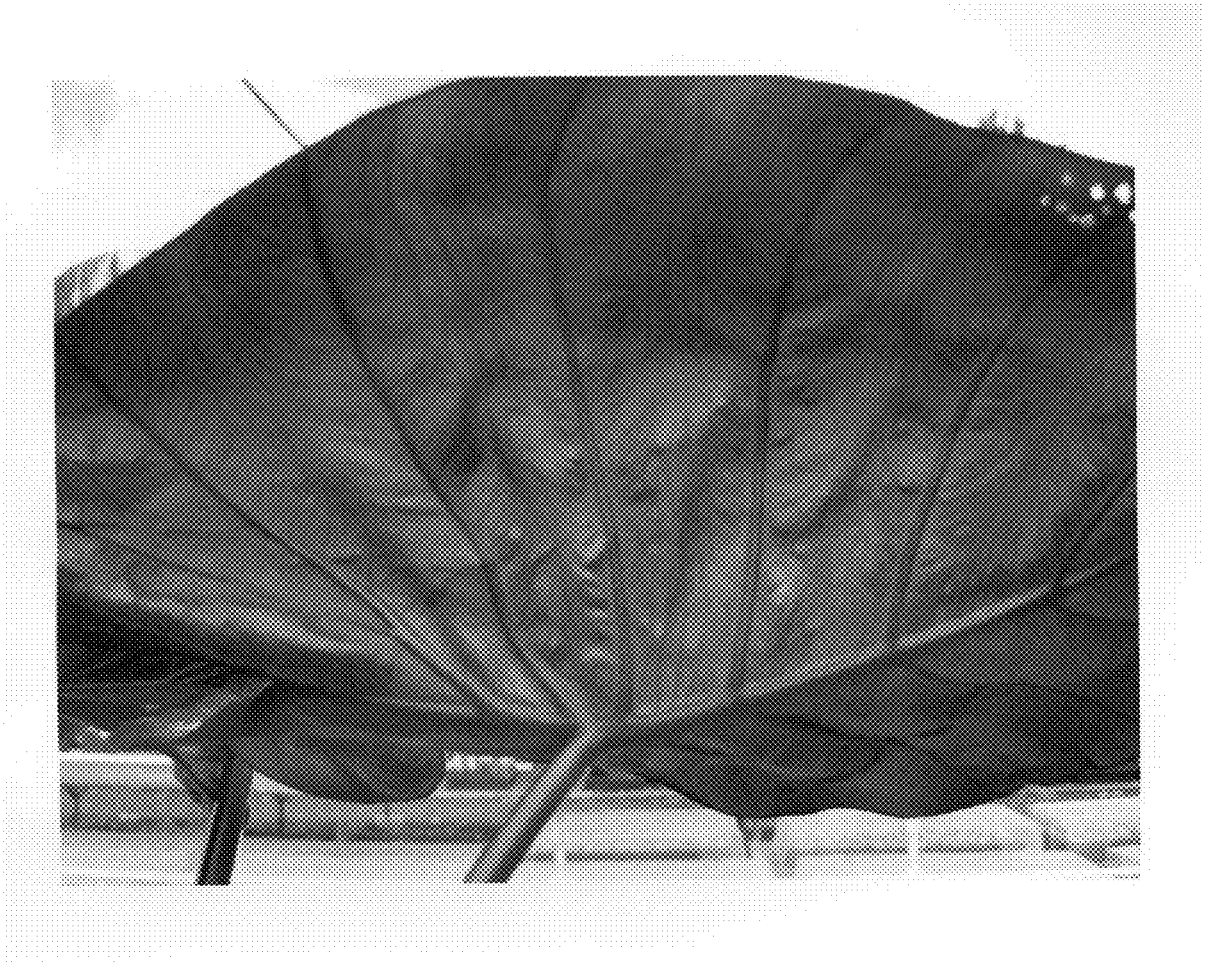

The drawing labeled as FIG. 4 shows the underside of a mature leaf of 'KONA COFFEE' with its light purple lamina and burgundy venation.

All drawings have been made from plants which were approximately 3 months old from a division and which have been grown out-of-doors. No growth regulators have been applied.

BOTANICAL DESCRIPTION OF THE PLANT

The following is a detailed description of the new *Colocasia* plant named 'KONA COFFEE'. Data was collected from plants that were 3-6 months of age grown outside in Kula, Hi. as indicated. The color determinations are in accordance with the 2001 edition of The Royal Horticultural Society Colour Chart, London, England, except where general color terms of ordinary dictionary significance are used. The growing requirements are similar to other *Colocasia*.

Botanical classification:
- *Genus.*—*Colocasia.*
- *Species.*—*esculenta.*

Denomination: 'KONA COFFEE'

Common name: Taro or elephant ears

Plant use: Food, container or landscape plant.

Cultural requirements: Cultural requirements are well draining soil or growing media, full sun to partial shade.

Root system: Fibrous.

Plant vigor: Vigorous.

Parentage:
- *Female parent.*—Inventor's unreleased seedling known as '2002-26'.
- *Male parent.*—Inventor's unreleased seedling known as '2005-51'.

Plant description: The plant has 4-7 suckers closely attached to the mother plant. A "mother plant" is the plant material which is first introduced into the soil to begin production. Typically, this plant material contains part of the huli and 2-3 leaf blades. This produces a "mother corm" which produces lateral shoots called 'cormels' which give rise to daughter plants. Daughter plants begin to appear above soil level about 2-3 months after planting of the mother plant.

Plant dimensions: Height -600 mm to 650 mm; width -540 mm to 670 mm.

Plant hardiness: USDA Zone 7b.

Propagation: Asexual propagation is accomplished by the excision and replanting of a plant shoot which consists of the apical 1cm-2 cm portion of the plant corm with the attached basal 15 cm-20 cm portion of the petiole. In regions of the world where *Colocasias* are grown, this plant shoot is known as a "huli", and the means of propagation is known as "huli propagation". Asexual reproduction has also been successfully achieved using the method of tissue culture.

Rooting from huli propagation: Root formation occurs immediately after transplanting. Propagation is complete when full rooted daughter plants appear above soil level around 2-3 months after huli planting.

Rooting from tissue culture: Root formation is rapid. A new plant is capable of growing on its own roots in approximately 3 weeks.

Crop time (from propagation to a saleable 1 gallon container): 6-10 weeks at air and soil temperatures of 65 degrees Fahrenheit. Pest or disease susceptibility and resistance: None known to the inventor.

Tuberous roots (mother corms):
- *Shape.*—Ovate.
- *Dimensions.*—4.5 cm-6.5 cm in length; 4.0 cm-4.4 cm in diameter.
- *Surface.*—Thin papery cortex, mostly smooth, color ranges between 168C and 178A.
- *Flesh.*—Texture farinaceous, color 155B.

Foliage:
- *Number.*—On average, a 5-6 month old mother plant maintains 6-8 functional leaves at a time; each new leaf is produced approximately every 10 days until the corm matures.
- *Petioles.*—Length: Up to 57 cm in length. Width: 5 mm immediately below the attachment to lamina; 10 mm measured at the upper sinus; 15 mm measured at the middle of the sinus. Color: Mature leaf has a petiole color of 187A and younger leaves have petiole color of 177D. Sap color: Colorless.

Leaf:
- *Dimensions at maturity* (5-6 *months old*).—355 mm in length and 235 mm in width.
- *Aspect.*—Erect with apex down.
- *Shape.*—Sagittate lamina.
- *Margins.*—Entire.
- *Apex.*—Pointed.
- *Base.*—Peltate.
- *Lamina appendages.*—Absent.
- *Attachment.*—Petiolate with characteristic tissue formed at junction of leaf blade with the upper termination of the petiole. This area of leaf tissue is also known as the 'piko'.
- *Piko appearance.*—Small, roughly circular with diameter 6 mm-8 mm; same color (187A) as the veins or darker. The principal veins radiate from the piko.
- *Leaf sheaf.*—Open.
- *Texture.*—Glossy.
- *Leaf color* (*abaxial surface*).—Younger leaves are 138B and mature leaves are 147B.
- *Leaf color* (*adaxial surface*).—Younger leaves are 198A and mature leaves are N187A.
- *Venation.*—Palmate.

*Veins*.—Three principal veins radiating from the piko with the largest a midrib extending from the piko to the tip of the lamina with up to 9 pairs of secondary veins radiating from it.

*Vein color* (*adaxial surface*).—187A.

*Vein color* (*abaxial surface*).—187A.

Flowers and reproductive organs: No flowers have been produced to date.

The invention claimed is:

1. A new and distinct cultivar of *Colocasia* plant named 'KONA COFFEE' as described and illustrated herein.

* * * * *